(12) United States Patent
Yamamoto et al.

(10) Patent No.: US 12,086,050 B2
(45) Date of Patent: Sep. 10, 2024

(54) ANALYSIS SYSTEM, SERVER APPARATUS, CONTROL METHOD, AND COMPUTER READABLE RECORDING MEDIUM

(71) Applicant: Shimadzu Corporation, Kyoto (JP)

(72) Inventors: Koki Yamamoto, Kyoto (JP); Noriyuki Ojima, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 539 days.

(21) Appl. No.: 17/352,887

(22) Filed: Jun. 21, 2021

(65) Prior Publication Data

US 2022/0058108 A1 Feb. 24, 2022

(30) Foreign Application Priority Data

Aug. 20, 2020 (JP) .................. 2020-139326

(51) Int. Cl.
*G06F 11/34* (2006.01)
*G01N 35/00* (2006.01)
(Continued)

(52) U.S. Cl.
CPC ... *G06F 11/3495* (2013.01); *G01N 35/00623* (2013.01); *G01N 35/00871* (2013.01);
(Continued)

(58) Field of Classification Search
USPC ........................................ 702/183
See application file for complete search history.

(56) References Cited

U.S. PATENT DOCUMENTS

| 7,925,461 B2 * | 4/2011 | Yamaguchi | G16H 40/40 700/109 |
| 8,246,907 B2 * | 8/2012 | Maeda | G16H 10/40 422/63 |

(Continued)

FOREIGN PATENT DOCUMENTS

| JP | 2000-266756 A | 9/2000 |
| JP | 2008-32751 A | 2/2008 |

(Continued)

OTHER PUBLICATIONS

Office Action issued Jul. 4, 2023 in Japanese Application No. 2020-139326.

(Continued)

*Primary Examiner* — Paul D Lee
(74) *Attorney, Agent, or Firm* — Sughrue Mion, PLLC

(57) ABSTRACT

An analysis system includes an analysis apparatus that analyzes a specimen managed in an analysis center and a server apparatus managed in a service center. A server apparatus stores a first reference specimen ID for identifying a first reference specimen and a first range based on a first reference value, in association with each other. The analysis apparatus analyzes the first reference specimen provided without notification of the first reference value and transmits to the server apparatus, the first reference specimen ID and an analytical value of the first reference specimen with which the first reference specimen ID is associated. When the server apparatus determines the received analytical value of the first reference specimen as not belonging to the first range stored in association with the received first reference specimen ID, the server apparatus provides an abnormality signal.

10 Claims, 8 Drawing Sheets

(51) Int. Cl.
  *G06F 11/07* (2006.01)
  *G06F 11/30* (2006.01)
  *G16H 10/40* (2018.01)
  *G16H 50/20* (2018.01)
  *G16H 40/60* (2018.01)

(52) U.S. Cl.
  CPC ...... *G06F 11/0709* (2013.01); *G06F 11/0751* (2013.01); *G06F 11/079* (2013.01); *G06F 11/3006* (2013.01); *G16H 10/40* (2018.01); *G16H 50/20* (2018.01); *G16H 40/60* (2018.01)

(56) References Cited

U.S. PATENT DOCUMENTS

2016/0356801 A1* 12/2016 Glavina ................. G16H 10/40
2022/0034922 A1*  2/2022 Singh ............... G01N 35/00712

FOREIGN PATENT DOCUMENTS

| JP | 2012-248217 A | 12/2012 |
| JP | 2019-039896 A | 3/2019 |

OTHER PUBLICATIONS

Japanese Office Action dated Sep. 26, 2023 in Japanese Application No. 2020-139326.

* cited by examiner

FIG.4

| ID | TYPE | RANGE |
|---|---|---|
| 1 | QC SAMPLE | Y1~Y2(SECOND RANGE) |
| 2 | SPECIMEN | Z1~Z2(THIRD RANGE) |
| 3 | SPECIMEN | Z1~Z2(THIRD RANGE) |
| ⋮ | ⋮ | ⋮ |
| 11 | QC SAMPLE | Y1~Y2(SECOND RANGE) |
| 12 | SPECIMEN | Z1~Z2(THIRD RANGE) |
| 13 | SPECIMEN | Z1~Z2(THIRD RANGE) |
| ⋮ | ⋮ | ⋮ |
| 48 | QC SAMPLE | Y1~Y2(SECOND RANGE) |
| 49 | VERIFICATION SAMPLE | X1~X2(FIRST RANGE) |
| 50 | SPECIMEN | Z1~Z2(THIRD RANGE) |

FIG.7

| ANALYSIS APPARATUS ID | DATE OF OCCURRENCE OF ABNORMALITY |
|---|---|
| 200A1 | Oct. 13, 2019 |
| 200A2 | NONE |
| 200A3 | Feb. 10, 2019 |
| ⋮ | ⋮ |

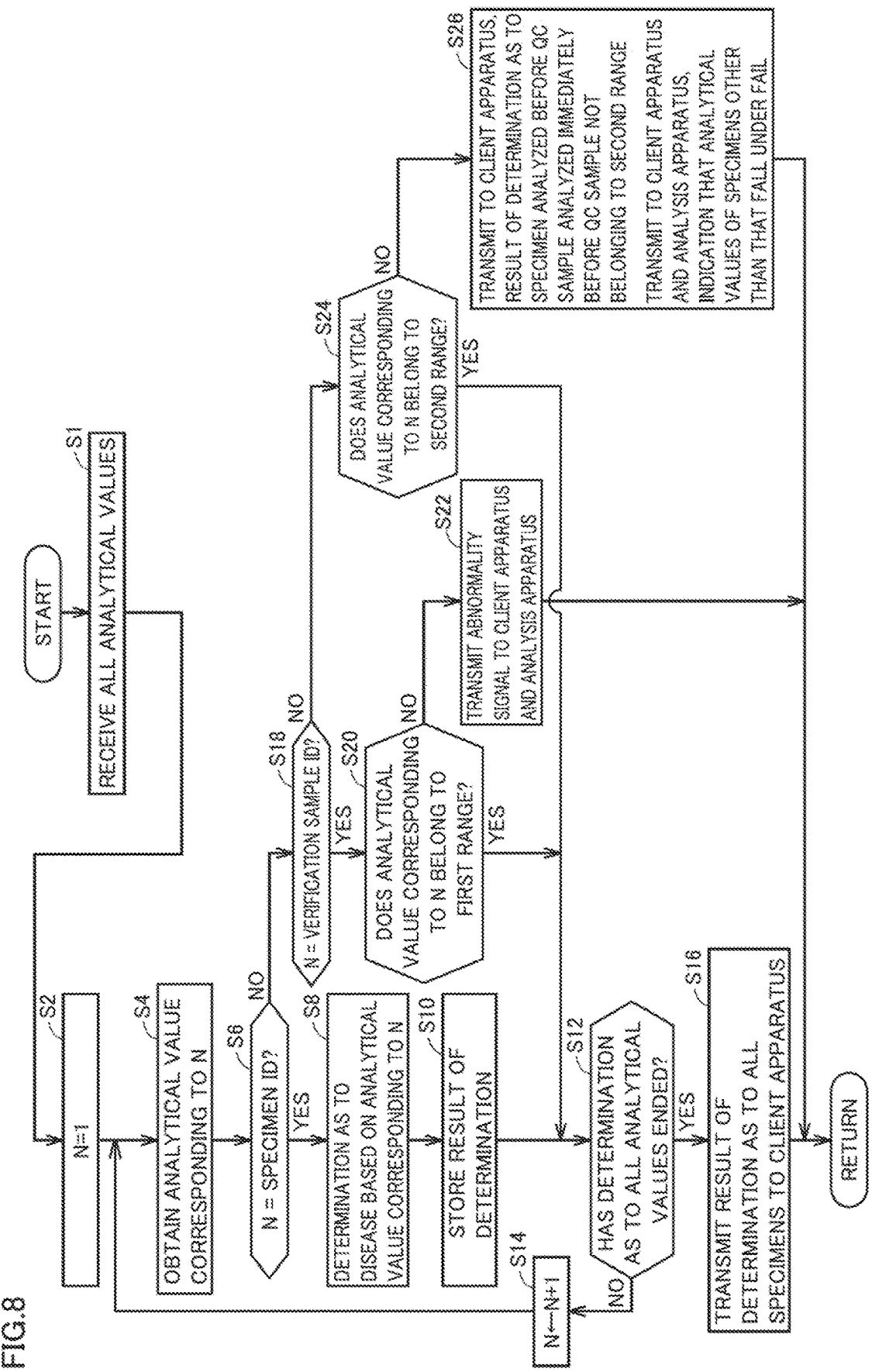

ANALYSIS SYSTEM, SERVER APPARATUS, CONTROL METHOD, AND COMPUTER READABLE RECORDING MEDIUM

BACKGROUND OF THE INVENTION

Field of the Invention

The present invention relates to an analysis system, a server apparatus, a control method, and a computer readable recording medium.

Description of the Background Art

Japanese Patent Laying-Open No. 2019-39896 has proposed an analysis system that analyzes a specimen taken from a subject, the analysis system including an analysis apparatus arranged in an analysis center and a server apparatus arranged in a service center. In this analysis system, the analysis apparatus transmits an analytical value obtained by analysis of the specimen to the server apparatus. The server apparatus makes determination as to a disease based on the received analytical value. The server apparatus transmits a result of determination to a terminal apparatus held by the subject.

SUMMARY OF THE INVENTION

An approach to evaluation of an analytical value obtained by analysis of a system verification sample is available as a method of appropriate determination as to abnormality in a series of analysis processes in an analysis system. When the analysis apparatus determines the analytical value of the system verification sample as belonging to a normal range, the analysis system is determined as being appropriate. When the analysis apparatus determines the analytical value of the system verification sample as not belonging to the normal range, the analysis system is determined as being abnormal.

Thus, in order to ensure quality of analysis by the analysis apparatus, it is important to analyze the system verification sample other than the specimen and to evaluate the analytical value thereof. In a configuration in which the analysis apparatus analyzes a sample and this analysis apparatus evaluates an analytical value thereof, a user of the analysis apparatus may tamper a result of evaluation of the analytical value. This tampering means, for example, disguising an analytical value of a system verification sample as belonging to the normal range in spite of the fact that the analytical value does not belong to the normal range. If such tampering is made, abnormality in the series of analysis processes in the analysis system cannot appropriately be detected.

The present invention was made to solve a problem as above, and an object thereof is to provide a technique allowing detection of abnormality in a series of analysis processes in an analysis system.

An analysis system according to one aspect of the present disclosure includes a plurality of analysis apparatuses each managed in at least one first facility, each of the plurality of analysis apparatuses analyzing a specimen of a subject, and a server apparatus managed in a second facility, the server apparatus being configured to communicate with the plurality of analysis apparatuses. The server apparatus stores a first reference specimen ID for identifying a first reference specimen for which a first reference value of a test item has been set and a first range based on the first reference value, in association with each other. Each of the plurality of analysis apparatuses analyzes the first reference specimen provided without notification of the first reference value and transmits an analytical value of the first reference specimen in association with the first reference specimen ID. When the server apparatus determines the received analytical value of the first reference specimen as not belonging to the first range corresponding to the received first reference specimen ID, the server apparatus provides an abnormality signal.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 4 is a diagram showing an exemplary table.

FIG. 7 is a diagram showing a date on which abnormality in each of a plurality of analysis apparatuses has occurred.

FIG. 8 shows an exemplary flowchart of processing performed in a controller of the server apparatus.

DESCRIPTION OF THE PREFERRED EMBODIMENTS

Figure 1:
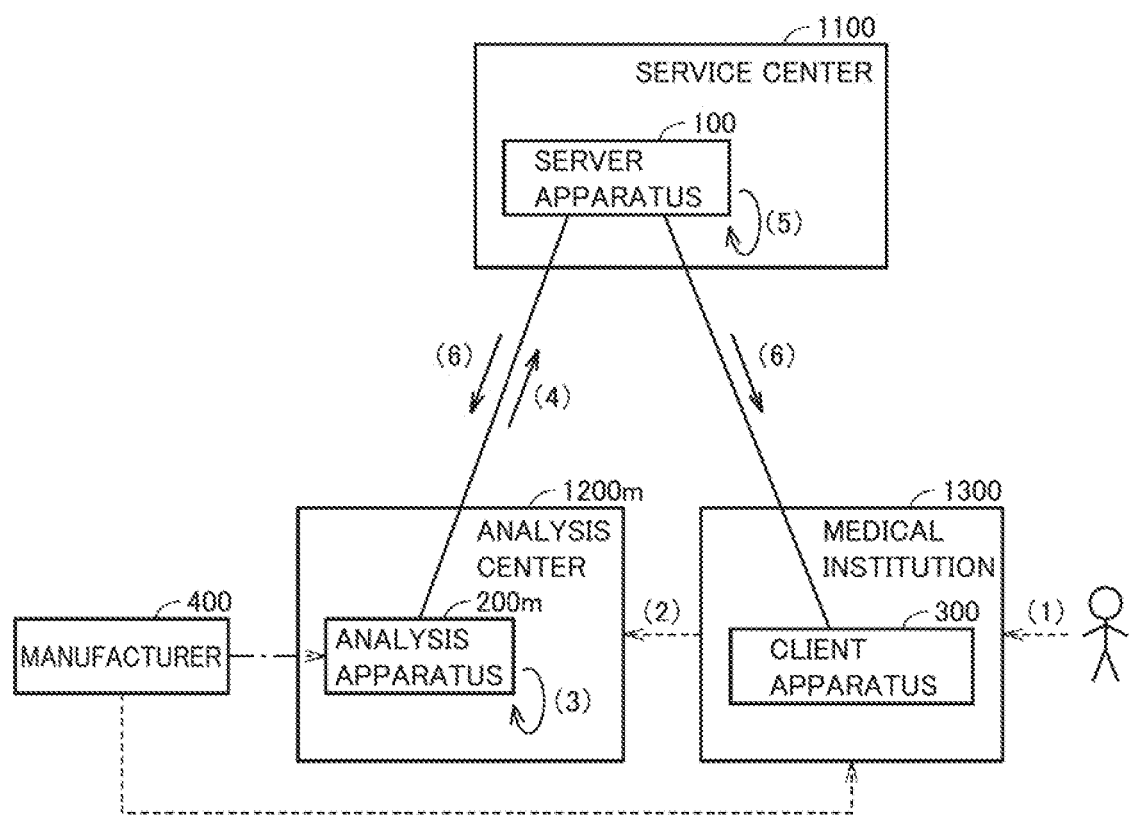
FIG. 1 is a diagram showing an exemplary configuration of an analysis system according to the present embodiment.

An embodiment of the present disclosure will be described in detail below with reference to the drawings. The same or corresponding elements in the drawings have the same reference characters allotted and description thereof will not be repeated.

[Overall Configuration of Analysis System]

FIG. 1 is a diagram showing an exemplary configuration of an analysis system 500 according to the present embodiment. Referring to FIG. 1, analysis system 500 includes a server apparatus 100, M (M being an integer equal to or larger than two) analysis apparatuses 200m (m=1, . . . , and M), and a client apparatus 300. A "plurality of analysis apparatuses 200m" may simply be referred to as an "analysis apparatus 200" below. FIG. 1 shows a single analysis apparatus 200m representing the "plurality of analysis apparatuses 200m" for brevity of illustration. Each of the plurality of analysis apparatuses 200m is provided with an analysis apparatus identification (ID) for identifying the analysis apparatus. Server apparatus 100 can individually recognize analysis apparatus 200 based on the analysis apparatus ID.

Server apparatus 100 is provided and managed in a service center 1100. Service center 1100 in the present embodiment represents an exemplary "second facility" in the present disclosure. Analysis apparatus 200 is provided and managed in an analysis center 1200. Analysis center 1200 represents an exemplary "first facility" in the present disclosure.

Client apparatus 300 is provided in a medical institution 1300. A person in charge in service center 1100 (who is also referred to as a user of server apparatus 100 below) is present in service center 1100. A person in charge (who is also referred to as a user of analysis apparatus 200 below) in analysis center 1200 is present in analysis center 1200.

Service center 1100 and analysis center 1200 are facilities different from each other. The person in charge in service center 1100 can objectively determine whether or not abnormality has occurred in a series of analysis processes in the analysis system based on a result of determination by server apparatus 100, regardless of opinions from the person in charge in analysis center 1200.

A person in charge (who is also referred to as a user of client apparatus 300 below) in medical institution 1300 is present in medical institution 1300. Analysis system 500 in the present embodiment serves to make determination as to at least one of whether or not a subject has a disease and a type of the disease by analyzing a specimen of the subject.

Server apparatus 100 and analysis apparatus 200 are communicatively connected to a network (a network 550 in FIG. 2), and they are configured to communicate with each other. Server apparatus 100 and client apparatus 300 are communicatively connected to the network (network 550 in FIG. 2), and they are configured to communicate with each other.

Analysis apparatus 200 analyzes a specimen of a subject. Examples of the specimen of the subject include blood of the subject. Any apparatus capable of analyzing the specimen of the subject may be applicable as analysis apparatus 200. Examples of analysis apparatus 200 include a liquid chromatograph, a gas chromatograph, a liquid chromatograph mass spectrometer, a gas chromatograph mass spectrometer, a scanning electron microscope, a transmission electron microscope, an energy dispersive X-ray fluorescence analyzer, a wavelength dispersive X-ray fluorescence analyzer, and a Fourier transform infrared spectrophotometer. Examples of analysis apparatus 200 may further include a photodiode array detector, a liquid chromatography tandem mass spectrometer, a gas chromatography tandem mass spectrometer, a liquid chromatograph mass spectrometer, a near infrared spectrophotometer, a tensile tester, and a compression tester.

Server apparatus 100 receives from analysis apparatus 200, an analytical value of a specimen obtained by analysis by analysis apparatus 200. Server apparatus 100 makes determination as to at least one of whether or not a subject from which the specimen was taken has a disease and a type of the disease of the subject, based on the analytical value. Determination as to at least one of whether or not the subject has a disease and the type of the disease corresponds to a "test item" in the present disclosure. Server apparatus 100 transmits a result of determination to client apparatus 300. In the present embodiment, a concentration of a prescribed substance contained in a specimen is employed as the analytical value. Another indicator such as a mass of a prescribed substance or a ratio of a mass (that is, a mass ratio) of a prescribed substance contained in a specimen to the mass of the specimen per one unit mass may be employed as the analytical value.

Client apparatus 300 shows the result of determination transmitted from server apparatus 100. The person in charge in medical institution 1300 notifies the subject of the result of determination.

A flow from taking of the specimen from the subject to notification of the subject of the result of determination based on the specimen will now be described with reference to FIG. 1. A solid arrow in FIG. 1 shows a flow of information and a dashed arrow shows a flow of a specimen or the like.

Initially, client apparatus 300 transmits an ID generation request to server apparatus 100 in response to an operation onto client apparatus 300 by the person in charge in medical institution 1300. The ID generation request transmitted from client apparatus 300 is information for having server apparatus 100 generate a specimen ID and a verification sample ID which will be described later. The person in charge in medical institution 1300 enters a type (information indicating either the specimen or the verification sample) for which an ID should be generated in response to the ID generation request and the number of IDs to be generated under this type. For example, when the person in charge in medical institution 1300 desires generation of thirty specimen IDs and one verification sample ID, he/she enters information indicating generation by server apparatus 100 of thirty specimen IDs and one verification sample ID into client apparatus 300.

When server apparatus 100 receives the ID generation request, it generates the specimen IDs for identifying the specimen and the verification sample ID for identifying the verification sample. Server apparatus 100 transmits the specimen IDs and the verification sample ID to client apparatus 300. The person in charge in medical institution 1300 attaches a label with the specimen ID transmitted from server apparatus 100 to a container. The verification sample ID will be described later. The specimen ID, a quality control (QC) sample ID which will be described later, and the verification sample ID may be given, for example, as any of a numbered label, a bar code label, and a radio frequency identifier (RFID).

In a step (1), the specimen of the subject is taken in medical institution 1300. Then, in a step (2), the container containing the specimen is provided from medical institution 1300 to analysis center 1200. Then, in a step (3), analysis apparatus 200 obtains an analytical value by analyzing the specimen.

Then, in a step (4), analysis apparatus 200 transmits the analytical value obtained as a result of analysis by analysis apparatus 200 to server apparatus 100. Then, in a step (5), server apparatus 100 determines based on the analytical value of the specimen, whether or not the subject from which the specimen was taken has a disease. Then, in a step (6), server apparatus 100 transmits a result of determination to client apparatus 300. Then, the subject is notified of the result of determination through medical institution 1300.

An approach to checking of accuracy of the analytical value obtained by analysis apparatus 200 with the use of a QC sample is available. The QC sample refers, for example, to a sample in which a prescribed substance (a marker) used for determination as to a disease has been mixed at a predetermined concentration. The person in charge or the like in analysis center 1200 prepares the QC sample. The user of the analysis apparatus is notified in advance of the concentration of the prescribed substance in the QC sample. An information processing apparatus (not shown) annexed to analysis apparatus 200 transmits an ID generation request to server apparatus 100 in response to an operation onto the information processing apparatus by the person in charge in analysis center 1200. For example, a personal computer (PC) or the like is adopted as the information processing apparatus.

The ID generation request transmitted from the information processing apparatus annexed to analysis apparatus 200 is information for having server apparatus 100 generate an ID of the QC sample (which is also referred to as a QC sample ID below). The person in charge in analysis center 1200 enters a type (a type indicating the QC sample) for which an ID should be generated in response to the ID generation request and the number of IDs to be generated for this type. For example, when the person in charge in analysis center 1200 desires generation of three QC sample IDs, he/she enters information indicating generation by server apparatus 100 of three QC sample IDs into the information processing apparatus.

When server apparatus 100 receives the ID generation request, it generates the QC sample IDs. Server apparatus 100 transmits the QC sample IDs to the information processing apparatus annexed to analysis apparatus 200.

The user of analysis apparatus 200 analyzes the QC sample with analysis apparatus 200, thereafter analyzes at least one specimen, and further analyzes the QC sample. Analysis apparatus 200 transmits an analytical value of the QC sample obtained as a result of analysis of the QC sample in the step (4). In the step (5), server apparatus 100 determines whether or not the analytical value of the QC sample belongs to the normal range. When the analytical value of the QC sample does not belong to the normal range, some abnormality may have occurred in analysis apparatus 200 after analysis of the QC sample analyzed immediately before the QC sample. Therefore, when the user of the analysis apparatus determines the analytical value of the QC sample as not belonging to the normal range, the user determines the analytical value of the specimen analyzed after the QC sample analyzed immediately before the QC sample as fail. When the analytical value of the QC sample does not belong to the normal range, in the step (6), server apparatus 100 transmits the ID of the specimen determined as fail to analysis apparatus 200 and client apparatus 300. The QC sample corresponds to the "second reference specimen" in the present disclosure.

In a test using the QC sample, however, only accuracy of the analytical value obtained by analysis apparatus 200 is simply checked, and abnormality in the series of analysis processes in analysis system 500 cannot be detected.

Analysis system 500 in the present embodiment detects whether or not abnormality has occurred in the series of analysis processes in analysis system 500. The series of analysis processes refers, for example, to a process from arrangement of samples by an operator in analysis center 1200 for conducting analysis and start of analysis by analysis apparatus 200 until transmission of an analytical value obtained in analysis to server apparatus 100. Examples of abnormality in the series of analysis processes include an error in systematic arrangement of samples by the operator, abnormality in an analysis function of analysis apparatus 200, and abnormality in a function to transmit an analytical value from analysis apparatus 200 to server apparatus 100 which will be described later.

A manufacturer 400 of analysis apparatus 200 makes a verification sample and provides the verification sample to medical institution 1300. The verification sample is a sample for detecting whether or not abnormality has occurred in the series of analysis processes in the analysis system. The verification sample refers to a sample in which a prescribed substance (a marker) used for determination as to a disease is mixed at a predetermined concentration. The verification sample corresponds to the "first reference specimen" in the present disclosure. The QC sample and the verification sample may be equal to or different from each other in concentration of the prescribed substance. The verification sample may be made in another facility instead of manufacturer 400. Examples of another facility include a subcontracting company or a group business of manufacturer 400.

As described above, server apparatus 100 generates a verification sample ID in response to an ID generation request from client apparatus 300. The verification sample ID is an ID for identification of the verification sample. The specimen ID, the verification sample ID, and the QC sample ID are stored as a table (see a table 1068 in FIG. 4) in a storage of server apparatus 100. This table is stored in the storage of server apparatus 100 for each analysis apparatus ID.

Server apparatus 100 receives a concentration of a prescribed substance in the verification sample from manufacturer 400. The verification sample ID and a first range based on the concentration of the prescribed substance in the verification sample are stored in server apparatus 100 in association with each other. Server apparatus 100 receives the concentration of the prescribed substance in the QC sample from analysis center 1200. The QC sample ID and a second range based on the concentration of the prescribed substance in the QC sample are stored in server apparatus 100 in association with each other. The specimen ID and a third range of the concentration of the prescribed substance contained in the specimen are stored in server apparatus 100 in association with each other.

As described above, server apparatus 100 transmits the verification sample ID to client apparatus 300. Server apparatus 100 may transmit the specimen ID and the verification sample ID to an apparatus different from client apparatus 300, so long as this apparatus is provided in medical institution 1300.

The person in charge in medical institution 1300 attaches a label showing the verification sample ID transmitted from server apparatus 100 to a container. The person in charge in medical institution 1300 places the verification sample in the container to which the label showing the verification sample ID has been attached.

In the step (2), the container containing the verification sample is provided from medical institution 1300 to analysis center 1200, together with the container containing the specimen. Analysis apparatus 200 receives the verification sample in a manner indistinguishable from the specimen. This manner is, for example, such that the container containing the specimen is identical to the container containing the verification sample and the label showing the specimen ID is identical to the label showing the verification sample ID. Thus, with the container containing the verification sample being mixed among a plurality of containers each containing the specimen, the container containing the verification sample is provided to analysis center 1200, together with the containers each containing the specimen.

In the step (3), analysis apparatus 200 obtains the analytical value of the verification sample by analyzing the verification sample. The user of analysis apparatus 200 can distinguish the QC sample from the specimen and the verification sample. Since analysis apparatus 200 receives the verification sample in the manner indistinguishable from the specimen, the user of analysis apparatus 200 is unable to distinguish between the specimen and the verification sample. In other words, the user of analysis apparatus 200 recognizes the container containing the verification sample as the container containing the specimen.

In the step (4), the analytical value of the verification sample is transmitted in association with the verification sample ID. In the step (4), analysis apparatus 200 may also transmit order information indicating the order of analysis of the specimen, the QC sample, and the verification sample to server apparatus 100. "The specimen ID, the analytical value of the specimen with which the specimen ID is associated, the QC sample ID, the analytical value of the QC sample with which the QC sample ID is associated, the verification sample ID, and the analytical value of the verification sample with which the verification sample ID is associated" are comprehensively referred to as "all analytical values" below. The all analytical values in the present embodiment correspond to all IDs (in the present embodiment, IDs=1 to 50 as shown in FIG. 4) generated by server apparatus 100.

In the step (5), server apparatus 100 determines whether or not abnormality has occurred in the series of analysis processes in the analysis system based on the analytical value of the verification sample with which the verification sample ID is associated.

When determination based on the analytical value of the verification sample indicates occurrence of abnormality in the series of analysis processes in analysis system 500, server apparatus 100 notifies in the step (5) that abnormality has occurred in the series of analysis processes in the analysis system performed by the analysis apparatus corresponding to the table in the first range used in this determination. This notification is given, for example, by providing an abnormality signal to a display (not shown) of server apparatus 100 to show an image showing occurrence or abnormality in the series of analysis processes on the display. The person in charge of server apparatus 100 thus recognizes occurrence of abnormality in the series of analysis processes in the analysis system performed by the analysis apparatus.

Furthermore, in the step (6), the abnormality signal is transmitted to analysis apparatus 200 corresponding to the table in the first range used in determination in the step (5). The abnormality signal indicates occurrence of abnormality in the series of analysis processes in analysis system 500. Analysis apparatus 200 that has received the abnormality signal gives a notification of occurrence or abnormality in the series of analysis processes. For example, analysis apparatus 200 has a display (not shown) thereof show an image showing occurrence of abnormality in the series of analysis processes. The user of analysis apparatus 200 can thus recognize occurrence of abnormality in analysis apparatus 200. When analysis apparatus 200 receives the abnormality signal, it may stop processing for analyzing the specimen that is being performed. In addition, server apparatus 100 transmits the abnormality signal to client apparatus 300.

[Exemplary Hardware Configuration of Server Apparatus]

Figure 2:
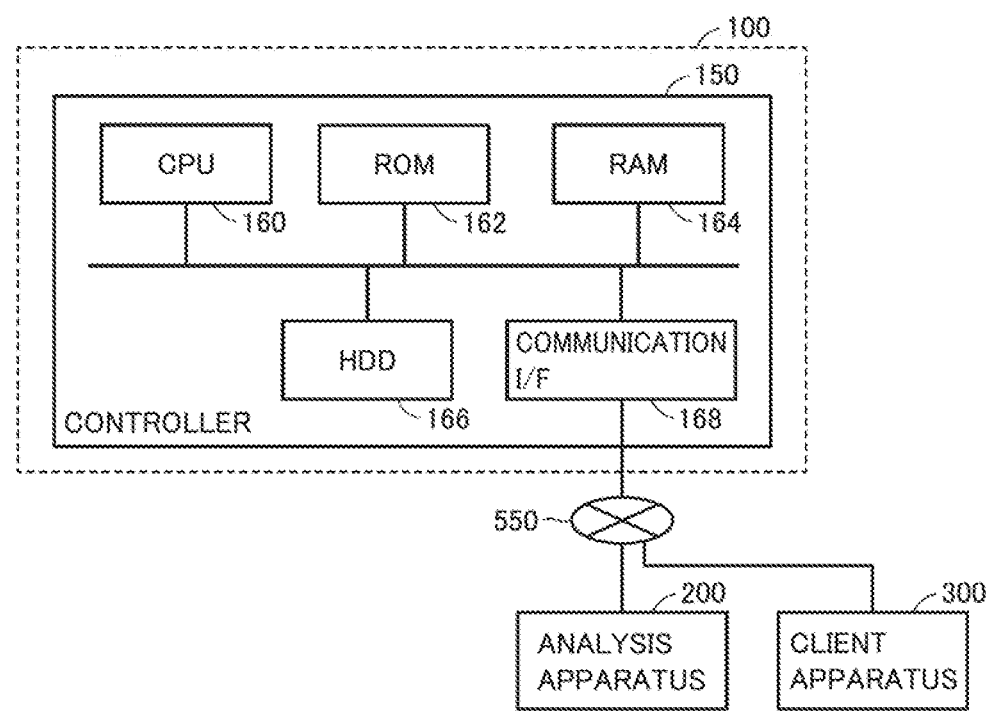
FIG. 2 is a diagram showing an exemplary hardware configuration of a server apparatus.

FIG. 2 is a diagram showing an exemplary hardware configuration of server apparatus 100. Server apparatus 100 includes a controller 150. Controller 150 includes, as its main components, a central processing unit (CPU) 160, a read only memory (ROM) 162, a random access memory (RAM) 164, a hard disk drive (HDD) 166, and a communication interface (I/F) 168. The components are connected to one another through a data bus.

Communication I/F 168 can communicate with analysis apparatus 200 and client apparatus 300 over network 550.

A program executed by CPU 160 is stored in ROM 162. Data generated by execution of a program by CPU 160 and data provided through communication I/F 168 can temporarily be stored in RAM 164. RAM 164 can function as a temporary data memory to be used as a work area. HDD 166 is a non-volatile storage apparatus. Instead of HDD 166, a semiconductor storage apparatus such as a flash memory may be adopted.

The program stored in ROM 162 may be distributed as a program product as being stored in a recording medium. Alternatively, the program may be provided by an information provider as a program product that can be downloaded through what is called the Internet. Server apparatus 100 reads a program provided from the recording medium or through the Internet. The read program is stored in a prescribed storage area (for example, ROM 162) in server apparatus 100. CPU 160 performs representation processing described above by executing the stored program.

The recording medium is not limited to a digital versatile disk read only memory (DVD-ROM), a compact disc read-only memory (CD-ROM), a flexible disk (FD), or a hard disk, but may be a medium that carries a program in a fixed manner such as a magnetic tape, a cassette tape, an optical disc (a magnetic optical disc (MO)/a mini disc (MD)/a digital versatile disc (DVD)), an optical card, or a semiconductor memory such as a mask ROM, an electronically programmable read-only memory (EPROM), an electronically erasable programmable read-only memory (EEPROM), or a flash ROM. The recording medium is a non-transitory medium from which a computer can read a program or the like.

[Functional Block Diagram of Analysis Apparatus and Server Apparatus]

Figure 3:
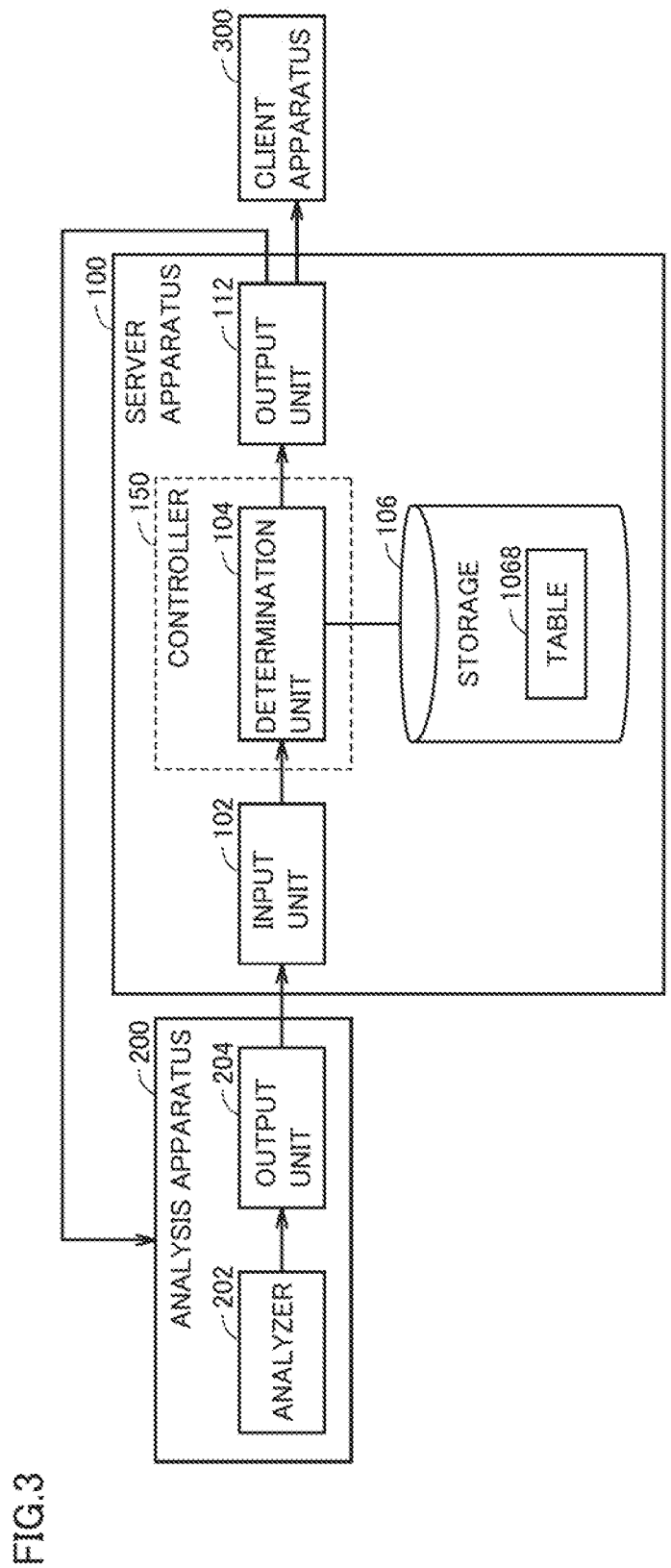
FIG. 3 is an exemplary functional block diagram of an analysis apparatus and the server apparatus.

FIG. 3 is an exemplary functional block diagram of analysis apparatus 200 and server apparatus 100. Analysis apparatus 200 includes an analyzer 202 and an output unit 204. Server apparatus 100 the includes an input unit 102, a determination unit 104, an output unit 112, and a storage 106. Input unit 102 and output unit 112 are implemented by communication I/F 168. Determination unit 104 is implemented by controller 150. Storage 106 is implemented by ROM 162, RAM 164, or the like.

Analyzer 202 obtains an analytical value of a specimen, an analytical value of a QC sample, and an analytical value of a verification sample by analyzing each of the specimen, the QC sample, and the verification sample (see the step (3) in FIG. 1). Output unit 204 transmits the all analytical values (the specimen ID, the analytical value of the specimen with which the specimen ID is associated, the QC sample ID, the analytical value of the QC sample with which the QC sample ID is associated, the verification sample ID, and the analytical value of the verification sample with which the verification sample ID is associated) to server apparatus 100 (see the step (4) in FIG. 1). Each time output unit 204 obtains any one of the analytical value of the specimen, the analytical value of the QC sample, and the analytical value of the verification sample, it may provide the obtained analytical value to server apparatus 100. Alternatively, when output unit 204 obtains the all analytical values of the specimen, the QC sample, and the verification sample, it may collectively transmit the analytical values to server apparatus 100. As shown in FIG. 4 which will be described later, in the present embodiment, the all analytical values are analytical values of the specimen, the QC sample, and the verification sample fifty in total.

Input unit 102 accepts input of the all analytical values. Table 1068 is stored in storage 106. As described above, server apparatus 100 generates the specimen ID, the verification sample ID, and the QC sample ID, and the specimen ID, the verification sample ID, and the QC sample ID are stored in storage 106 as table 1068.

FIG. 4 is a diagram showing exemplary table 1068. As described above, table 1068 stores the type and the range for each analysis apparatus ID. In the example in FIG. 4, IDs 1 to 50 are defined. In other words, FIG. 4 shows an example in which the specimen, the QC sample, and the verification sample fifty in total are provided. In the example in FIG. 4, IDs=1, 11, and 48 are generated as the QC sample IDs, ID=49 is generated as the verification sample ID, and other IDs are generated as the specimen IDs.

Determination unit 104 determines a type of each of the all analytical values based on table 1068 and a plurality of IDs entered into input unit 102. In the example in FIG. 4, determination unit 104 determines the analytical values with which IDs=1, 11, and 48 are associated as the analytical values of the QC sample. Determination unit 104 determines the analytical value with which ID=49 is associated as the analytical value of the verification sample. Determination unit 104 determines the analytical values with which IDs other than IDs=1, 11, 48, and 49 are associated as the analytical values of the specimen.

Determination unit 104 performs determination processing by using a range corresponding to the type of the analytical value. In the present embodiment, the first range corresponds to the analytical value of the verification sample. The second range corresponds to the analytical value of the QC sample. The third range corresponds to the analytical value of the specimen.

The first range is determined based on a concentration of a prescribed substance (a substance used for determination as to a disease) mixed in the verification sample. The first range refers to a normal range of the analytical value of the verification sample and represents an allowable tolerance.

The first range is defined by an upper limit value calculated by adding a prescribed value to the concentration of the prescribed substance and a lower limit value calculated by subtracting the prescribed value from the concentration of the prescribed substance. For example, when the concentration of the prescribed substance mixed in the verification sample is 5% and the prescribed value is set to 0.2%, the first range is from 4.8% to 5.2%. "Five percent" corresponds to the first "reference value" in the present disclosure. The ratio from "4.8% to 5.2%" corresponds to the "first range based on the first reference value" in the present disclosure. FIG. 4 shows the first range as ranging from X1 to X2.

When analysis apparatus 200 analyzes the verification sample in which the concentration of the prescribed substance is 5% while analysis apparatus 200 is normal, it provides a value belonging to the first range as the analytical value. When analysis apparatus 200 analyzes this verification sample while there is abnormality in the series of analysis processes in analysis system 500, however, analysis apparatus 200 may provide a value not belonging to the first range as the analytical value. The value not belonging to the first range is a value larger than the upper limit value of the first range or smaller than the lower limit value of the first range.

For example, the analytical value obtained by analysis of verification sample by analysis apparatus 200 while there is abnormality in the analysis function of analysis apparatus 200 may not belong the first range. Alternatively, a transmission function of analysis apparatus 200 may be abnormal, although there is no abnormality in the analysis function of analysis apparatus 200. The transmission function refers to a function to transmit the analytical value obtained by the analysis function to server apparatus 100. When there is no abnormality in the analysis function of analysis apparatus 200, analysis apparatus 200 obtains a value belonging to the first range (for example, 5%) as the analytical value of the verification sample. When abnormality occurs in the transmission function, however, for example, the verification sample ID and the specimen ID may erroneously be transmitted as being interchanged. This case refers to a case in which the analytical value of the specimen (for example, 8%) is erroneously transmitted in association with the verification sample ID and the analytical value of the verification sample (for example, 5%) is erroneously transmitted in association with the specimen ID. In this case, determination unit 104 determines the analytical value (8%) of the specimen as not belonging to the first range. When the operator makes an error in systematic arrangement of samples as well, the analytical value obtained by analysis of the verification sample by analysis apparatus 200 may not belong to the first range. Abnormality in the series of analysis processes may include abnormality in at least one of a signal line from analysis apparatus 200 to network 550, network 550, a signal line from network 550 to server apparatus 100, and a reception function of server apparatus 100.

Thus, when the specimen (verification sample) associated with the verification sample ID does not belong to the first range, abnormality may have occurred in the series of analysis processes (for example, the analysis function or the transmission function).

The second range is determined based on the concentration or the prescribed substance mixed in the QC sample. The second range refers to a normal range of the analytical value of the QC sample and represents an allowable tolerance. The second range is defined by an upper limit value calculated by adding a prescribed value to the concentration of the prescribed substance and a lower limit value calculated by subtracting the prescribed value from the concentration of the prescribed substance. For example, when the concentration of the prescribed substance mixed in the verification sample is 7% and the prescribed value is set to 0.2%, the second range is from 6.8% to 7.2%. "Seven percent" corresponds to the "second reference value" in the present disclosure. The ratio from "6.8% to 7.2%" corresponds to the "second range based on the second reference value." FIG. 4 shows the second range as ranging from Y1 to Y2.

When analysis apparatus 200 analyzes the QC sample in which the concentration of the prescribed substance is 7% while the analysis function of analysis apparatus 200 is normal, analysis apparatus 200 provides a value belonging to the second range as the analytical value. When analysis apparatus 200 analyzes the QC sample while there is abnormality in the analysis function of analysis apparatus 200, however, analysis apparatus 200 provides a value not belonging to the second range as the analytical value. The value not belonging to the second range refers to a value larger than the upper limit value of the second range or smaller than the lower limit value of the second range. Processing when the analytical value of the QC sample does not belong to the second range will be described in detail with reference to FIG. 5.

The third range is used for the analytical value of the specimen. For example, when determination unit 104 determines the analytical value of the specimen as belonging to the third range, it determines the subject from which the specimen was taken as not having a disease. When determination unit 104 determines the analytical value of the specimen as not belonging to the third range, it determines the subject from which the specimen was taken as having a disease. Furthermore, while the analytical value of the specimen does not belong to the third range, when determination unit 104 determines the analytical value as belonging to a prescribed range, it may determine the subject from which the specimen was taken as having a first disease, and when it determines the analytical value as belonging to a specific range, it may determine the subject from which the specimen was taken as having a second disease. FIG. 4 shows the third range as ranging from Z1 to Z2.

Referring back to FIG. 3, when determination unit 104 determines the analytical value of the verification sample as not belonging to the first range, it has the display of server apparatus 100 show that abnormality has occurred in the series of analysis processes in the analysis system performed by analysis apparatus 200 corresponding to the table in the first range. This notification is given by output of the abnormality signal to the display of server apparatus 100. With this notification, the user or the like of server apparatus 100 can detect abnormality in the series of analysis processes in analysis system 500. Furthermore, determination unit 104 transmits the abnormality signal through output unit 112 to analysis apparatus 200 corresponding to the table in the first range (that is, analysis apparatus 200 that has transmitted the analytical value of the verification sample not belonging to the first range). Analysis apparatus 200 that has received the abnormality signal notifies that abnormality has occurred in the series of analysis processes. With this notification, the user or the like of analysis apparatus 200 can detect abnormality in the series of analysis processes in analysis system 500. When analysis apparatus 200 receives the abnormality signal, it may stop analysis of the specimen that is being conducted. Analysis of the specimen in analysis apparatus 200 where abnormality has occurred can thus be prevented.

When determination unit 104 determines the analytical value of the verification sample as belonging to the first range, it does not transmit the abnormality signal. When determination unit 104 determines the analytical value of the verification sample as belonging to the first range, it may transmit a normal signal indicating that the series of analysis processes is normal to analysis apparatus 200 through output unit 112.

Determination unit 104 transmits a result of determination based on the analytical value of the QC sample to analysis apparatus 200 and client apparatus 300 through output unit 112. Determination unit 104 transmits a result of determination based on the analytical value of the specimen to client apparatus 300 through output unit 112.

Thus, in the present embodiment, server apparatus 100 managed in service center 1100 rather than analysis apparatus 200 managed in analysis center 1200 can detect abnormality in the series of analysis processes based on an analytical value for system verification and the first range. Therefore, server apparatus 100 can detect abnormality in the series of analysis processes in the analysis system without the user or the like of the analysis apparatus tampering the result of evaluation of the analytical value of the first reference specimen. This tampering means, for example, disguising the analytical value of the system verification sample as be to the normal range in spite of the fact that the analytical value does not belong to the normal range.

In order to ensure accuracy in a test for a disease of a subject, analysis apparatus 200 should analyze a specimen while there is no abnormality in the series of analysis processes in analysis system 500. For such reasons as distribution of analysis centers 1200 over many areas and difficulty in securing staff familiar with determination of abnormality in the series of analysis processes, it is difficult for the user of analysis apparatus 200 to check whether or not abnormality has occurred in the series of analysis processes.

Since abnormality may have occurred in the series of analysis processes when the analytical value of the verification sample does not belong to the first range, analysis apparatus 200 that has received the abnormality signal gives a notification that abnormality in the series of analysis processes has occurred. Therefore, the user or the like of analysis center 1200 can recognize abnormality in the series of analysis processes in analysis system 500. Since analysis of a specimen by analysis apparatus 200 while there is abnormality in the series of analysis processes in analysis system 500 can be prevented, accuracy in a test for a disease of a subject can be ensured.

If the user of analysis apparatus 200 could distinguish between the container containing the specimen and the container containing the verification sample in analysis of the specimen and the verification sample by analysis apparatus 200, the user of analysis apparatus 200 may tamper the result of evaluation of the analytical value of the verification sample (or the analytical value). In view of such a situation, the container containing the specimen and the container containing the verification sample are provided from medical institution 1300 to analysis center 1200 in a manner indistinguishable by the user of analysis apparatus 200 and analysis apparatus 200. In other words, as described with reference to the step (2) in FIG. 1, analysis apparatus 200 receives the verification sample in the manner indistinguishable from the specimen. Therefore, server apparatus 100 can determine whether or not abnormality has occurred in the analysis apparatus without the user of analysis apparatus 200 being aware of checking as to occurrence of abnormality in analysis apparatus 200.

As described with reference to FIG. 1, the specimen is provided from medical institution 1300 to analysis center 1200. On the other hand, the verification sample is provided front manufacturer 400 to medical institution 1300 after it is made by manufacturer 400, and then provided from medical institution 1300 to analysis center 1200. Thus, the specimen and the verification sample are provided to analysis apparatus 200 through routes different from each other. Therefore, server apparatus 100 can determine whether or not abnormality has occurred in analysis apparatus 200 based on the analytical value of the verification sample provided through the route different from the route for the specimen, and hence the user of analysis apparatus 200 can make objective determination. Since server apparatus 100 can determine whether or not abnormality has occurred in analysis apparatus 200 based on the analytical value of the verification sample made by manufacturer 400, manufacturer 400 can provide analysis system 500 for which manufacturer 400 plays a dominant role.

The analytical values may be stored in table 1068 in server apparatus 100, in correspondence with ID1 to ID50 in FIG. 4. Whether or not the analytical value belongs to a corresponding range may be stored in table 1068 in server apparatus 100, in correspondence with ID1 to ID50 in FIG. 4. In other words, whether or not the analytical value of the verification sample belongs to the first range, whether or not the analytical value of the QC sample belongs to the second range, and whether or not the analytical value of the specimen belongs to the third range (that is, a disease) may be stored in table 1068 in server apparatus 100. Server apparatus 100 can thus manage a result of analysis by analysis apparatus 200 and whether or not the analytical value belongs to the corresponding range in a centralized manner. As will be described with reference to FIG. 7, when analysis system 500 includes a plurality of analysis apparatuses 200, an analytical value and whether or not the analytical value belongs to a corresponding range may be stored for each of the plurality of analysis apparatuses 200.

Each of the plurality of analysis apparatuses 200m may generate a specimen ID, a verification sample ID, and a QC sample ID. According to this configuration, however, analysis apparatuses 200 generate IDs belonging to different systems. Consequently, ID management becomes complicated, which may lead to tendency of errors in ID management. In the present embodiment, server apparatus 100 generates a specimen ID, a verification sample ID, and a QC sample ID for each of the plurality of analysis apparatuses 200m. Therefore, server apparatus 100 can manage in a centralized manner, the specimen ID, the verification sample ID, and the QC sample ID for each of the plurality of analysis apparatuses 200m. Furthermore, server apparatus 100 "detects abnormality in the series of analysis processes (determination with the use of the verification sample)," "makes determination with the use of the QC sample," and "makes determination as to at least one of whether or not a subject has a disease and a type of the disease." Therefore, analysis system 500 in the present embodiment can provide such a service that server apparatus 100 "generates the specimen ID, the verification sample ID, and the QC sample ID for each of the plurality of analysis apparatuses 200m," "detects abnormality in the series of analysis processes (determination with the use of the verification sample)," "makes determination with the use of the QC sample," and "makes determination as to at least one of whether or not a subject has a disease and a type of the disease."

[Analysis of QC Sample and Verification Sample]

Figure 5:
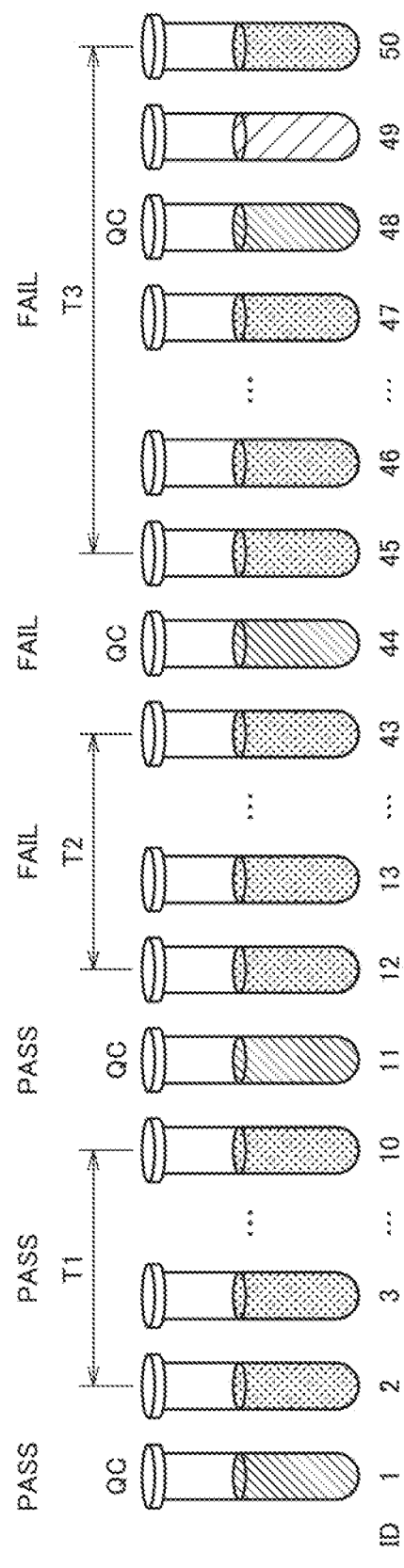
FIG. 5 is a diagram showing determination as to an analytical value of a QC sample by the server apparatus.

Details of determination as to the analytical value of the QC sample by server apparatus 100 will now be described. FIG. 5 is a diagram for illustrating determination as to an analytical value of the QC sample by server apparatus 100. In an example in FIG. 5 and FIG. 6 which will be described later, a specimen is shown with a dot pattern, a QC sample is shown with a hatching pattern rising toward top right, and a verification sample is shown with a hatching pattern falling toward bottom right. In the example in FIG. 5 and FIG. 6 which will be described later, the QC sample IDs 1, 11, 44, and 48 and the verification sample ID 49 are shown. The example in FIG. 5 shows that the analytical value of the verification sample belongs to the first range (that is, the analytical value of the verification sample is normal).

As described above, analysis apparatus 200 analyzes one QC sample, thereafter analyzes the verification sample or at least one specimen, and further analyzes one QC sample. FIG. 5 shows an example in which determination unit 104 (see FIG. 3) determines the analytical value of the QC sample having the QC sample ID=44 as fail. In this case, determination unit 104 determines as fail, the analytical values of the specimens (having IDs=12 to 43 and 45 to 50) analyzed after the QC sample (the QC sample having the QC sample ID=11) analyzed immediately before the QC sample (having the QC sample ID=44) that has been determined as fail.

As shown in FIG. 5, server apparatus 100 can determine whether or not the analytical value of the specimen falls under pass, by using a QC sample different from the verification sample.

Figure 6:
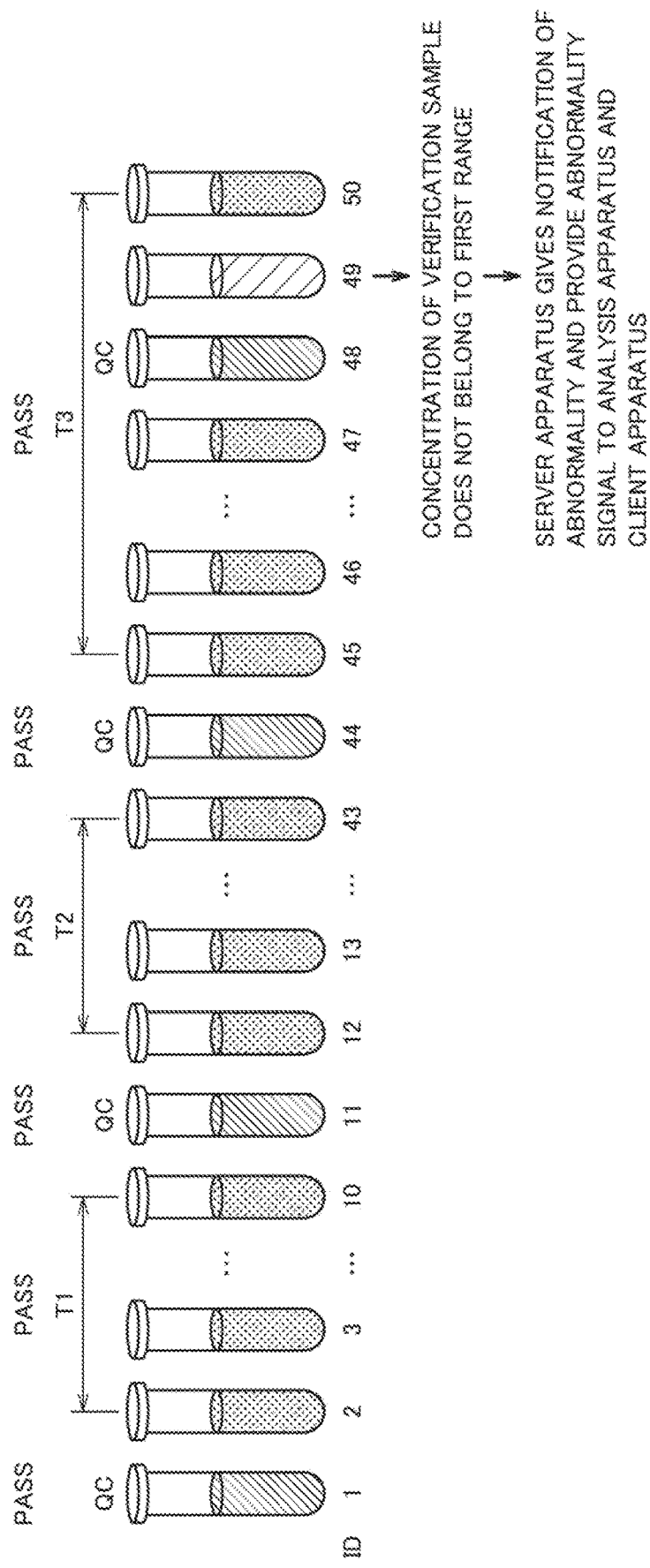
FIG. 6 is a diagram showing determination as to an analytical value of a verification sample by the server apparatus.

FIG. 6 shows an example in which the analytical value of the verification sample does not belong to the first range (that is, the analytical value of the verification sample is abnormal). FIG. 6 shows the example in which the analytical value of each of all QC samples falls under pass.

As shown in FIG. 6, when determination unit 104 determines the analytical value of the verification sample as not belonging to the first range, determination unit 104 determines analysis apparatus 200 as being abnormal and server apparatus 100 gives a notification of abnormality and provides the abnormality signal to analysis apparatus 200 and client apparatus 300.

[Management of Analysis Apparatus by Server Apparatus]

Management of analysis apparatus 200 by server apparatus 100 will now be described. Server apparatus 100 may manage whether or not abnormality has occurred in a series of analysis steps in each of the plurality of analysis apparatuses 200m. FIG. 7 is a diagram showing a date on which abnormality in each of the plurality of analysis apparatuses 200m has occurred. As shown in FIG. 7, an analysis apparatus ID is set for each of the plurality of analysis apparatuses 200m. In the example in FIG. 7, analysis apparatus IDs 200A1, 200A2, 200A3, . . . are set for the plurality of analysis apparatuses 200m, respectively. The analysis apparatus IDs are provided as reference numerals for the plurality of analysis apparatuses 200m below. Server apparatus 100 holds a table shown in FIG. 7.

FIG. 7 shows an example in which abnormality occurred in analysis apparatus 200A1 on Oct. 13, 2019. FIG. 7 shows an example in which no abnormality occurred in analysis apparatus 200A2. FIG. 7 shows an example in which abnormality occurred in analysis apparatus 200A3 on Feb. 10, 2019.

As shown in FIG. 7, for each of the plurality of analysis apparatuses 200, occurrence of abnormality in analysis apparatus 200 is stored in server apparatus 100. Therefore, the manager or the like of server apparatus 100 can know whether or not abnormality has occurred in each of the plurality of analysis apparatuses 200. Though not shown in FIG. 7, the analytical value of the specimen provided from the analysis apparatus may be stored in server apparatus 100 for each analysis apparatus. Whether the analytical value of the QC sample falls under pass or fail may be stored in server apparatus 100.

[Flowchart of Processing Performed in Controller 150]

FIG. 8 shows an exemplary flowchart of processing performed in controller 150 of server apparatus 100. In FIG. 8, the specimen ID, the verification sample ID, and the QC sample ID are comprehensively denoted as "N". N is a numeric value shown in the order information described above.

Initially, in step S1, server apparatus 100 receives all analytical values. Then, in step S2, controller 150 sets N to an initial value ("1" in the example in FIG. 8). In step S4, controller 150 obtains an analytical value corresponding to N from a plurality of analytical values. In step S6, controller 150 determines whether or not N represents the specimen ID. When the controller determines N as the specimen ID (YES in step S6), determination unit 104 in controller 150 makes determination as to a disease in step S8 based on the third range and the analytical value corresponding to N (that is, the analytical value of the specimen having the specimen ID=N). In step S10, controller 150 has a result of determination in step S8 stored in storage 106.

In step S12, controller 150 determines whether or not determination for all analytical values has totally ended. When the controller determines that determination as to all analytical values has ended (YES in step S12), in step S16, server apparatus 100 transmits a result of determination as to all specimens to client apparatus 300. When the controller determines that determination as to all analytical values has not ended (NO in step S12), in step S14, controller 150 increments N by one and the process returns to step S4.

When N is determined as not representing the specimen ID (NO in step S6), in step S18, controller 150 determines whether or not N represents the verification sample ID.

When N is determined as representing the verification sample ID (YES in step S18), in step S20, determination unit 104 in controller 150 determines whether or not the analytical value corresponding to N (that is, the analytical value of the verification sample) belongs to the first range (see FIG. 3). When the analytical value corresponding to N is determined as belonging to the first range (YES in step S20), the process proceeds to step S12. When the analytical value corresponding to N is determined as not belonging to the first range (NO in step S20), the process proceeds to step S22. In step S22, controller 150 gives a notification of abnormality. Concurrently, in step S22, controller 150 transmits the abnormality signal to analysis apparatus 200 and client apparatus 300. Analysis apparatus 200 notifies the user of analysis apparatus 200 of occurrence of abnormality therein. Client apparatus 300 notifies the person in charge in medical institution 1300 of occurrence of abnormality in analysis apparatus 200. Thereafter, the process ends.

When N is determined as representing neither of the specimen ID and the verification sample ID (NO in step S18), N is concluded as representing the QC sample ID. In this case, in step S24, determination unit 104 in controller 150 determines whether or not the analytical value corresponding to N (that is, the analytical value of the QC sample) belongs to the second range (see FIG. 3). When the analytical value corresponding to N is determined as belonging to the second range (YES in step S24), the process proceeds to step S12. When the analytical value corresponding to N is determined as not belonging to the second range (NO in step S24), the process proceeds to step S26.

As described with reference to FIG. 5, controller 150 transmits to client apparatus 300 in step S26, a result of determination as to the specimens (the specimens having the IDs=2 to 10 in FIG. 5) analyzed prior to analysis of the QC sample (having the ID=11 in FIG. 5) immediately before the QC sample (having the ID=44 in FIG. 5) the analytical value of which has been determined as not belonging to the second range. In step S26, controller 150 transmits to client apparatus 300 and analysis apparatus 200, information indicating that the analytical values of specimens (that is, the specimens having the IDs=12 to 43 and 45 to 49 in FIG. 5) other than those fall under fail. Client apparatus 300 notifies the person in charge in medical institution 1300 of the specimen IDs of the failed specimens based on this information.

As described with reference to FIG. 8, when the analytical value of the verification sample is determined as not belonging to the first range (NO in step S20), the processing in step S16 is not performed. Therefore, transmission by controller 150, of the result of analysis of the specimen to client apparatus 300 is restricted. Therefore, transmission from server apparatus 100 to client apparatus 300, of the result of determination obtained while there is abnormality in the series of analysis processes can be prevented.

When determination as NO is made in determination as to whether or not N represents the verification sample ID described with reference to step S18, controller 150 may determine whether or not N represents the QC sample ID. When determination as YES is made in this determination, the process proceeds to step S24. When determination as NO is made in this determination, server apparatus 100 may give an error notification. Determination as NO in this determination is made when an ID different from the ID generated by server apparatus 100 is transmitted to analysis apparatus 200. With this error notification, the user of server apparatus 100 can recognize transmission to analysis apparatus 200, of an ID different from the ID generated by server apparatus 100.

[Modification]

(1) A configuration in which the abnormality signal is provided from server apparatus 100 to analysis apparatus 200 is described in the embodiment above. The abnormality signal, however, may be provided to another apparatus. For example, an apparatus provided in service center 1100 may be defined as another apparatus. Another apparatus notifies the person in charge in service center 1100 or the like of occurrence of abnormality in analysis apparatus 200 when it receives the abnormality signal. The person in charge in service center 1100 notifies the user of analysis apparatus 200 of occurrence of abnormality in analysis apparatus 200 by an electronic mail or the like.

(2) A configuration in which the container containing the specimen and the container containing the verification sample are provided to analysis center 1200 in a manner indistinguishable by the user of analysis apparatus 200 and analysis apparatus 200 is described in the embodiment above. The container containing the specimen and the container containing the verification sample, however, may be provided to analysis center 1200 in such a manner that at least one of the user of analysis apparatus 200 and analysis apparatus 200 is able to distinguish between them.

(3) A configuration in which the specimen of the subject is taken in medical institution 1300 is described in the embodiment above (see FIG. 1 and the like). The subject himself/herself, however, may take the specimen (for example, sputum of the subject). In this case, an apparatus (for example, a smartphone or the like) held by the subject is defined as client apparatus 300. In this case, the verification sample is provided to analysis center 1200, with a provider of the verification sample being defined as a dummy subject.

A configuration in which server apparatus 100 transmits a result of determination as to the specimen to client apparatus 300 is described in the embodiment above. Server apparatus 100, however, may have the result of determination as to the specimen printed and the person in charge in service center 1100 may send paper on which the result of determination is printed to the subject by postal mail.

(4) A configuration in which the analysis apparatus analyzes one QC sample, thereafter analyzes the verification sample or at least one specimen, and further analyzes one QC sample is described in the embodiment above. In other words, with a period during which the analysis apparatus analyzes the verification sample or at least one specimen being defined as a "prescribed period," the analysis apparatus analyzes the QC sample each time the prescribed period elapses. Another period may be set as the prescribed period. For example, a temporal period may be set as the prescribed period. For example, one day may be set as the prescribed period.

(5) A configuration in which server apparatus 100 determines whether or not the analytical value of the QC sample belongs to the second range is described in the embodiment above. According to such a configuration, server apparatus 100 can collectively make determination as to the analytical value of the specimen, determination as to the analytical value of the QC sample, and determination as to the analytical value of the verification sample. A result of determination as to the analytical value of the specimen, a result of determination as to the analytical value of the QC sample, and a result of determination as to the analytical value of the verification sample can collectively be stored in server apparatus 100. In addition, analysis apparatus 200 may determine whether or not the analytical value of the QC sample belongs to the second range. According to such a configuration, when analysis apparatus 200 determines the analytical value of the QC sample as not belonging to the second range, analysis apparatus 200 may give a notification of abnormality. With the notification of abnormality, the user of analysis apparatus 200 can immediately recognize that abnormality therein may have occurred.

[Aspects]

Illustrative embodiments described above are understood by a person skilled in the art as specific examples of aspects below.

(Clause 1) An analysis system according to one aspect includes a plurality of analysis apparatuses each managed in at least one first facility, each of the plurality of analysis apparatuses analyzing a specimen of a subject, and a server apparatus managed in a second facility, the server apparatus being capable of communicating with the plurality of analysis apparatuses. The server apparatus stores a first reference specimen ID for identifying a first reference specimen for which a first reference value of a test item has been set and a first range based on the first reference value in association with each other. Each of the plurality of analysis apparatuses analyzes the first reference specimen provided without notification of the first reference value and transmits an analytical value of the first reference specimen in association with the first reference specimen ID. When the server apparatus determines the received analytical value of the first reference specimen as not belonging to the first range corresponding to the received first reference specimen ID, the server apparatus provides an abnormality signal.

According to the analysis system in Clause 1, when the server apparatus managed in the first facility determines the analytical value of the first reference specimen obtained by the analysis apparatus managed in the second facility as not belonging to the first range, it provides the abnormality signal. Therefore, abnormality in a series of analysis processes in the analysis system can be detected without tampering by the user or the like of the analysis apparatus on a result of determination as to the analytical value of the first reference specimen.

(Clause 2) In the analysis system described in Clause 1, each of the plurality of analysis apparatuses receives the first reference specimen in a manner indistinguishable from the specimen.

According to the analysis system in Clause 2, the analysis apparatus is unable to distinguish between the specimen and the first reference specimen. Therefore, abnormality in the series of analysis processes in the analysis system can be recognized without the user being aware of checking as to occurrence of abnormality in the analysis apparatus.

(Clause 3) In the analysis system in Clause 1 or 2, the abnormality signal is provided to the analysis apparatus that has transmitted the analytical value of the first reference specimen not belonging to the first range corresponding to the first reference specimen ID, and the analysis apparatus stops analysis of the specimen in response to reception of the abnormality signal.

According to the analysis system in Clause 3, the analysis apparatus can prevent analysis of the specimen therein while there is abnormality in the series of analysis processes in the analysis system.

(Clause 4) The analysis system described in any one of Clauses 1 to 3 includes an analysis apparatus different from the analysis apparatus, and for each analysis apparatus, the server apparatus stores occurrence of abnormality in that analysis apparatus.

According to the analysis system in Clause 4, the server apparatus can collectively manage for each analysis apparatus, occurrence of abnormality in the analysis apparatus.

(Clause 5) In the analysis system described in any one of Clauses 1 to 4, the specimen and the first reference specimen are provided to each of the plurality of analysis apparatuses through routes different from each other.

According to the analysis system in Clause 5, the server apparatus can make determination as to abnormality in the series of analysis processes in the analysis system with the use of the first reference specimen provided through the route different from the route for the specimen. Therefore, the server apparatus can make objective determination.

(Clause 6) In the analysis system described in any one of Clauses 1 to 5, the first reference specimen is made by a manufacturer of the analysis apparatuses.

According to the analysis system in Clause 6, the server apparatus can determine occurrence of abnormality in the analysis apparatus with the use of the analytical value of the first reference specimen made by the manufacturer of the analysis apparatuses. Therefore, the manufacturer of the analysis apparatuses can provide the analysis system for which the manufacturer of the analysis apparatuses plays a dominant role.

(Clause 7) In the analysis system described in any one of Clauses 1 to 6, each of the plurality of analysis apparatuses analyzes the specimen and transmits the analytical value of the specimen to the server apparatus in association with a specimen ID for identifying the specimen. When the server apparatus determines the received analytical value of the first reference specimen as not belonging to the first range corresponding to the received first reference specimen ID, the server apparatus restricts notification of a result of analysis of the specimen to the subject.

According to the analysis system in Clause 7, transmission to client apparatus 300, of a result of determination obtained while there is abnormality in the series of analysis processes can be prevented.

(Clause 8) In the analysis system described in any one of Clauses 1 to 7, the server apparatus stores a second reference specimen ID for identifying a second reference specimen for which a second reference value of the test item has been set and a second range based on the second reference value in association with each other. Each of the plurality of analysis apparatuses analyzes the second reference specimen provided with notification of the second reference value and transmits an analytical value of the second reference specimen in association with the second reference specimen ID. When the server apparatus determines the received analytical value of the second reference specimen as not belonging to the second range corresponding to the received second reference specimen ID, the server apparatus determines the analytical value of the specimen analyzed after analysis of the second reference specimen immediately before the second reference specimen as fail.

According to the analysis system in Clause 8, accuracy of the analytical value of the specimen can be checked with the use of a second reference sample different from a first reference sample.

(Clause 9) A server apparatus included in the analysis system described in any one of Clauses 1 to 8.

According to the server apparatus in Clause 9, when the server apparatus determines the analytical value of the first reference specimen for which the first reference value of the test item has been set as not belonging to the first range based on the first reference value, it provides the abnormality signal. Therefore, the user or the like of the analysis apparatus can recognize abnormality in the series of analysis processes in the analysis system.

(Clause 10) A control method according to one aspect is a method of controlling a server apparatus. The server apparatus is capable of communicating with a plurality of analysis apparatuses each managed in at least one first facility, each of the plurality of analysis apparatuses analyzing a specimen of a subject. The server apparatus stores a first reference specimen ID for identifying a first reference specimen for which a first reference value of a test item has been set and a first range based on the first reference value, in association with each other. The server apparatus is managed in a second facility. The control method includes receiving the first reference specimen ID and an analytical value of the first reference specimen with which the first reference specimen ID is associated and providing an abnormality signal when the received analytical value of the first reference specimen is determined as not belonging to the first range corresponding to the received first reference specimen ID.

According to the control method in Clause 10, when the server apparatus managed in the first facility determines the analytical value of the first reference specimen obtained by the analysis apparatus managed in the second facility as not belonging to the first range, it provides the abnormality signal. Therefore, abnormality in the series of analysis processes in the analysis system can be detected without tampering by the user or the like of the analysis apparatus on the result of determination as to the analytical value of the first reference specimen.

(Clause 11) A computer readable recording medium according to one aspect is a computer readable recording medium having a program for controlling a computer recorded thereon. The computer is capable of communicating with a plurality of analysis apparatuses each managed in at least one first facility, each of the plurality of analysis apparatuses analyzing a specimen of a subject. The computer stores a first reference specimen ID for identifying a first reference specimen for which a first reference value of a test item has been set and a first range based on the first reference value, in association with each other. The computer is managed in a second facility. The program causes the computer to perform receiving the first reference specimen ID and an analytical value of the first reference specimen with which the first reference specimen ID is associated and providing an abnormality signal when the received analytical value of the first reference specimen is determined as not belonging to the first range corresponding to the received first reference specimen ID.

According to the control program in Clause 11, when the computer managed in the first facility determines the analytical value of the first reference specimen obtained by the analysis apparatus managed in the second facility as not belonging to the first range, it provides the abnormality signal. Therefore, abnormality in the series of analysis processes in the analysis system can be detected without tampering by the user or the like of the analysis apparatus on the result of determination as to the analytical value of the first reference specimen.

The embodiment disclosed herein is also intended to be carried out as being combined as appropriate within the technically consistent scope. It should be understood that the embodiment disclosed herein is illustrative and non-restrictive in every respect. The scope of the present embodiment is defined by the terms of the claims rather than the description of the embodiment above and is intended to include any modifications within the scope and meaning equivalent to the terms of the claims.

What is claimed is:

1. An analysis system comprising:
   a plurality of analysis apparatuses each managed in at least one first facility, each of the plurality of analysis apparatuses being configured to analyze a specimen of a subject; and
   a server apparatus managed in a second facility, the server apparatus being configured to communicate with the plurality of analysis apparatuses, wherein
   the server apparatus is further configured to store a first reference specimen ID for identifying a first reference specimen for which a first reference value of a test item has been set and a first range based on the first reference value, in association with each other,
   each of the plurality of analysis apparatuses are further configured to:
   analyze the first reference specimen provided without notification of the first reference value, and
   transmit, to the server apparatus, an analytical value of the first reference specimen in association with the first reference specimen ID,
   the server apparatus is further configured to receive the analytical value of the first reference specimen in association with the first reference specimen ID and to provide an abnormality signal to the analysis apparatus in a state in which the server apparatus determines the analytical value of the first reference specimen as not belonging to the first range corresponding to the first reference specimen ID,
   the first reference specimen is contained in a first container with a first label showing the first reference specimen ID,
   the specimen is contained in a specimen container with a specimen label showing a specimen ID,
   each of the plurality of analysis apparatuses is further configured to receive the first reference specimen in a manner indistinguishable from the specimen, and
   the manner is such that the first container and the specimen container are identical and the first label showing the first reference specimen ID and the specimen label showing specimen ID are identical.

2. The analysis system according to claim 1, wherein
   the server apparatus provides the abnormality signal to an analysis apparatus that has transmitted the analytical value of the first reference specimen not belonging to the first range corresponding to the first reference specimen ID, and
   the analysis apparatus stops analysis of the specimen in response to reception of the abnormality signal.

3. The analysis system according to claim 1, wherein
   for each of the plurality of analysis apparatuses, the server apparatus stores the number of occurrences of abnormality signals provided to each of the plurality of analysis apparatuses.

4. The analysis system according to claim 1, wherein
   the specimen and the first reference specimen are provided to each of the plurality of analysis apparatuses through routes different from each other.

5. The analysis system according to claim 1, wherein
   the first reference specimen is made by a manufacturer of the analysis apparatuses.

6. The analysis system according to claim 1, wherein
   each of the plurality of analysis apparatuses are further configured to analyze the specimen, and transmit the analytical value of the specimen to the server apparatus in association with a specimen ID for identifying the specimen, and in a state in which the server apparatus determines the received analytical value of the first reference specimen as not belonging to the first range corresponding to the received first reference specimen ID, the server apparatus is further configured to restricts notification of a result of analysis of the specimen to the subject.

7. The analysis system according to claim 1, wherein the server apparatus being further configured to store a second reference specimen ID for identifying a second reference specimen for which a second reference value of the test item has been set and a second range based on the second reference value, in association with each other, each of the plurality of analysis apparatuses are further configured to:

analyze the second reference specimen provided with notification of the second reference value, and transmit, to the server apparatus, an analytical value of the second reference specimen in association with the second reference specimen ID, the server apparatus is further configured to:

receive the analytical value of the second reference specimen in association with the second reference specimen ID;

determine the analytical value of the second reference specimen as fail in a state in which the server apparatus determines the received analytical value of the second reference specimen as not belonging to the second range corresponding to the received second reference specimen ID; and in a state in which the analytical value of the second reference specimen is determined as fail, determine an analytical value of a specimen analyzed after the second reference specimen as fail and an analytical value of a specimen analyzed immediately before the second reference specimen as fail.

8. A server apparatus included in the analysis system according to claim 1.

9. A method of controlling a server apparatus by at least one processor, the server apparatus being configured to communicate with a plurality of analysis apparatuses each managed in at least one first facility, each of the plurality of analysis apparatuses being configured to analyze a specimen of a subject, the specimen being contained in a specimen container with a specimen label showing a specimen ID, the server apparatus being further configured to store a first reference specimen ID for identifying a first reference specimen for which a first reference value of a test item has been set and a first range based on the first reference value, in association with each other, the first reference specimen being contained in a first container with a first label showing the first reference specimen ID, the server apparatus being managed in a second facility, the method comprising:

receiving, by the server apparatus from one of the each of the plurality of analysis apparatuses, the first reference specimen ID and an analytical value of the first reference specimen with which the first reference specimen ID is associated;

receiving, by each of the plurality of analysis apparatuses, the first reference specimen in a manner indistinguishable from the specimen, and the manner is such that the first container and the specimen container are identical and the first label showing the first reference specimen ID and the specimen label showing specimen ID are identical; and providing, by the server apparatus, an abnormality signal in a state in which the received analytical value of the first reference specimen is determined as not belonging to the first range corresponding to the received first reference specimen ID.

10. A non-transitory computer readable recording medium having a program for controlling a computer recorded thereon, the computer being configured to communicate with a plurality of analysis apparatuses each managed in at least one first facility, each of the plurality of analysis apparatuses are configured to analyze a specimen of a subject, the specimen being contained in a specimen container with a specimen label showing a specimen ID, the computer is configured to store a first reference specimen ID for identifying a first reference specimen for which a first reference value of a test item has been set and a first range based on the first reference value, in association with each other, the first reference specimen being contained in a first container with a first label showing the first reference specimen ID, the computer being managed in a second facility, the program causing the computer to perform:

receiving, the first reference specimen ID and an analytical value of the first reference specimen with which the first reference specimen ID is associated;

receiving, by each of the plurality of analysis apparatuses, the first reference specimen in a manner indistinguishable from the specimen, and the manner is such that the first container and the specimen container are identical and the first label showing the first reference specimen ID and the specimen label showing specimen ID are identical; and providing an abnormality signal in a state in which the received analytical value of the first reference specimen is determined as not belonging to the first range corresponding to the received first reference specimen ID.

* * * * *